May 16, 1972 J. H. ASPER Plant Pat. 3,170
CAMELLIA HYBRID
Filed June 5, 1970
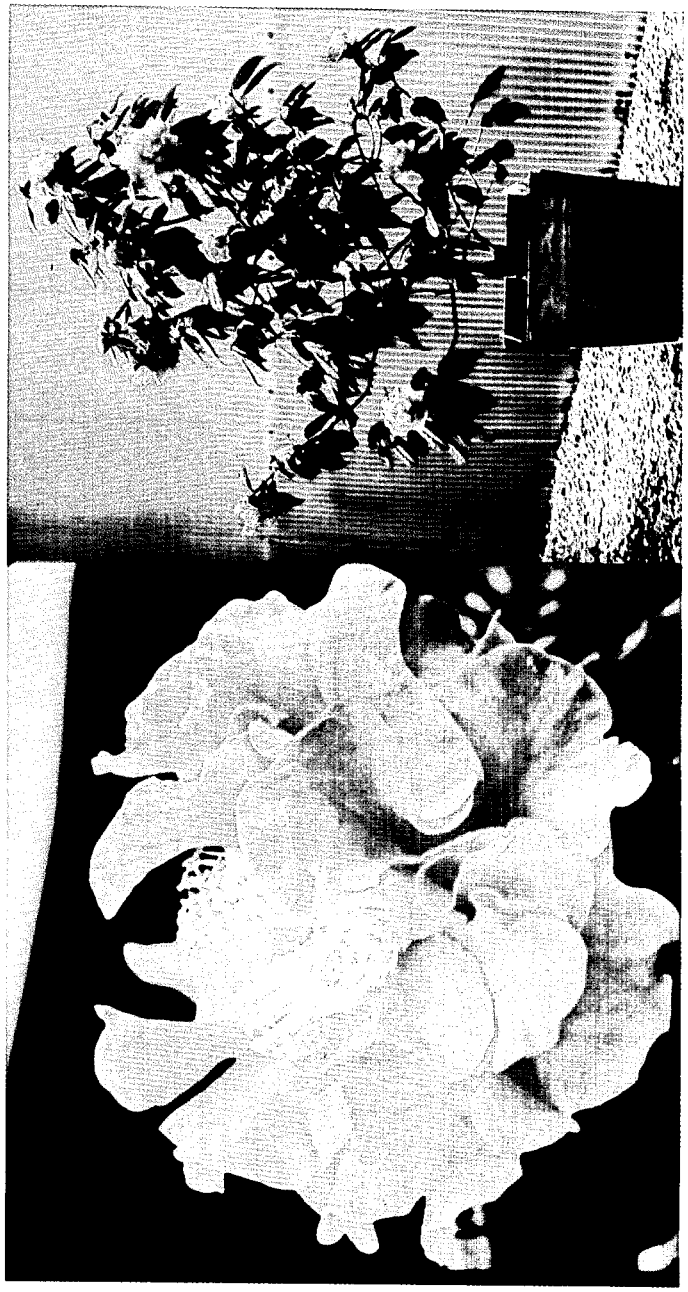
INVENTOR.
J. HOWARD ASPER,
By Edmond F. Shanahan
ATTORNEY.

United States Patent Office

Plant Pat. 3,170
Patented May 16, 1972

3,170

CAMELLIA HYBRID

J Howard Asper, Escondido, Calif., assignor to Monrovia Nursery Company, Azusa, Calif.

Filed June 5, 1970, Ser. No. 43,986
Int. Cl. A01h 5/00
U.S. Cl. Plt.—62 1 Claim

ABSTRACT OF THE DISCLOSURE

A new and distinct variety of camellia, originating as a seedling from a crossing of *Camellia reticulata* "Crimson Robe" (the seed parent) and *Camellia japonica* "Lotus" (the pollen parent). The new camellia is characterized as to novelty by its exceptionally large flower and its large coriaceous leaves.

The present discovery relates to a new and distinct variety of the genus Camellia, having a very large rose-colored flower.

I first produced the plant in the month of March, in the year 1959, as the result of prolonged breeding efforts. The plant appeared originally as a sport or seedling from *Camellia reticulata* "Crimson Robe" and *Camellia japonica* "Lotus."

All present plants have been reproduced asexually from the original plant of March 1959. The plant has never been offered for sale to the public. The plant has never been described in any publication.

As will be seen from the following description of the plant, it is clearly distinct and different from any known variety, and no known variety can be identified as bearing some substantial degree of similarity to it.

A detailed description of the plant follows, which may be read with reference to the accompanying color photographs of the flower and the whole plant. The British Horticultural Colour Charts are used, by reference, in the description of the colors found in the plant.

*The plant*

Parentage: The plant was the result of definite breeding efforts between *C. reticulata* "Crimson Robe" (the seed parent) and *C. japonica* "Lotus" (the pollen parent). The new plant first appeared in March 1959. It first flowered in March 1964.

Growth habit: The shrub exhibits an upright habit, with long, sturdy branches. The new wood is light brown, while the older bark is gray and shredding.

Foliage: The leaves are elliptic, 4 to 5 inches long and 1⅜ to 2¼ inches wide, with a petiole length of ¼ to 5/16 inch. The leaf is coriaceous in texture, sharply serrate, and with prominent veins. The tip is acuminate and the base is narrowly obtuse. The upper surface is Ivy Green 0001060/2 and the underside is Spinach Green 0960/2, in accordance with the British Horticultural Colour Charts.

Flower: The flower is very large, 6 to 7 inches across and 3¼ to 3½ inches deep. The petals are numerous, 18 to 21, 2½ to 3 inches in diameter and orbicular in shape, with a deeply notched apex and undulate margins. Stamens are numerous with three pistils joined. The color of the petals is Rose Madder 23/1, with the base of the petals Rose Madder 23/2, shading through Rose Madder 23/1 to the margins which are Rose Madder 23. Often a flower will be faintly marbled.

I claim:

1. A new and distinct variety of camellia hybrid as described.

No references cited.

ROBERT E. BAGWILL, Primary Examiner